United States Patent [19]
Sackier et al.

[11] Patent Number: 5,776,146
[45] Date of Patent: Jul. 7, 1998

[54] LAPAROSCOPIC SURGICAL CLAMP

[75] Inventors: Jonathan M. Sackier, Great Falls, Va.; Michael L. Jones, Capistrano Beach; Edward E. Dolendo, Huntington Beach, both of Calif.

[73] Assignee: Applied Medical Resources, Laguna Hills, Calif.

[21] Appl. No.: 674,925

[22] Filed: Jul. 3, 1996

Related U.S. Application Data

[63] Continuation-in-part of Ser. No. 139,919, Oct. 20, 1993, Pat. No. 5,496,333.

[51] Int. Cl.$^6$ ................................................. A61B 17/10
[52] U.S. Cl. ................................................. 606/142; 606/206
[58] Field of Search ................................ 606/142, 151, 606/143, 205, 206, 208, 139, 141

[56] References Cited

U.S. PATENT DOCUMENTS 5,176,699  1/1993  Markham ................................ 606/208
5,250,056  10/1993  Hasson ................................... 606/208

Primary Examiner—Michael Buiz
Assistant Examiner—Kevin Truong
Attorney, Agent, or Firm—Richard L. Myers

[57] ABSTRACT

A surgical clamp combination includes a clamp movable between a free state and operable state, the clamp including a pair of jaws which can be operated to occlude a body conduit. A clamp applier is adapted to releasably engage the clamp in the free state and to operate the clamp in the operable state to close the jaws. The applier has a housing disposed at a proximal end and a tube operable state. A first shaft is disposed within the tube and movable between an extended position to releasably hold the clamp in the operable state. With the clamp in the operable state, a second shaft is movable by operation of a handle, to alternatively move a pin in opposite directions, along a line normal to an axis of the second shaft, to open and close the jaws of the clamp.

35 Claims, 8 Drawing Sheets

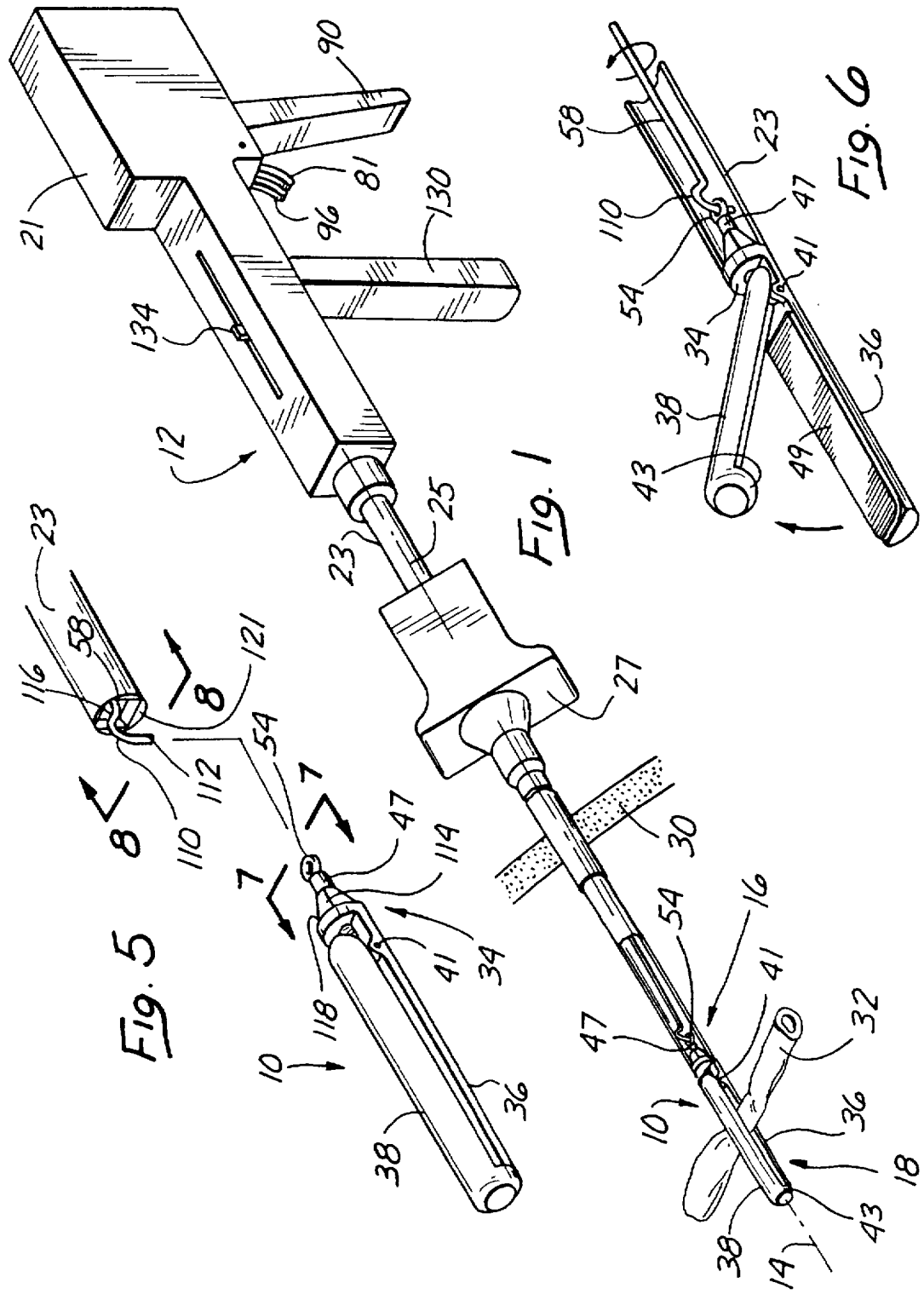

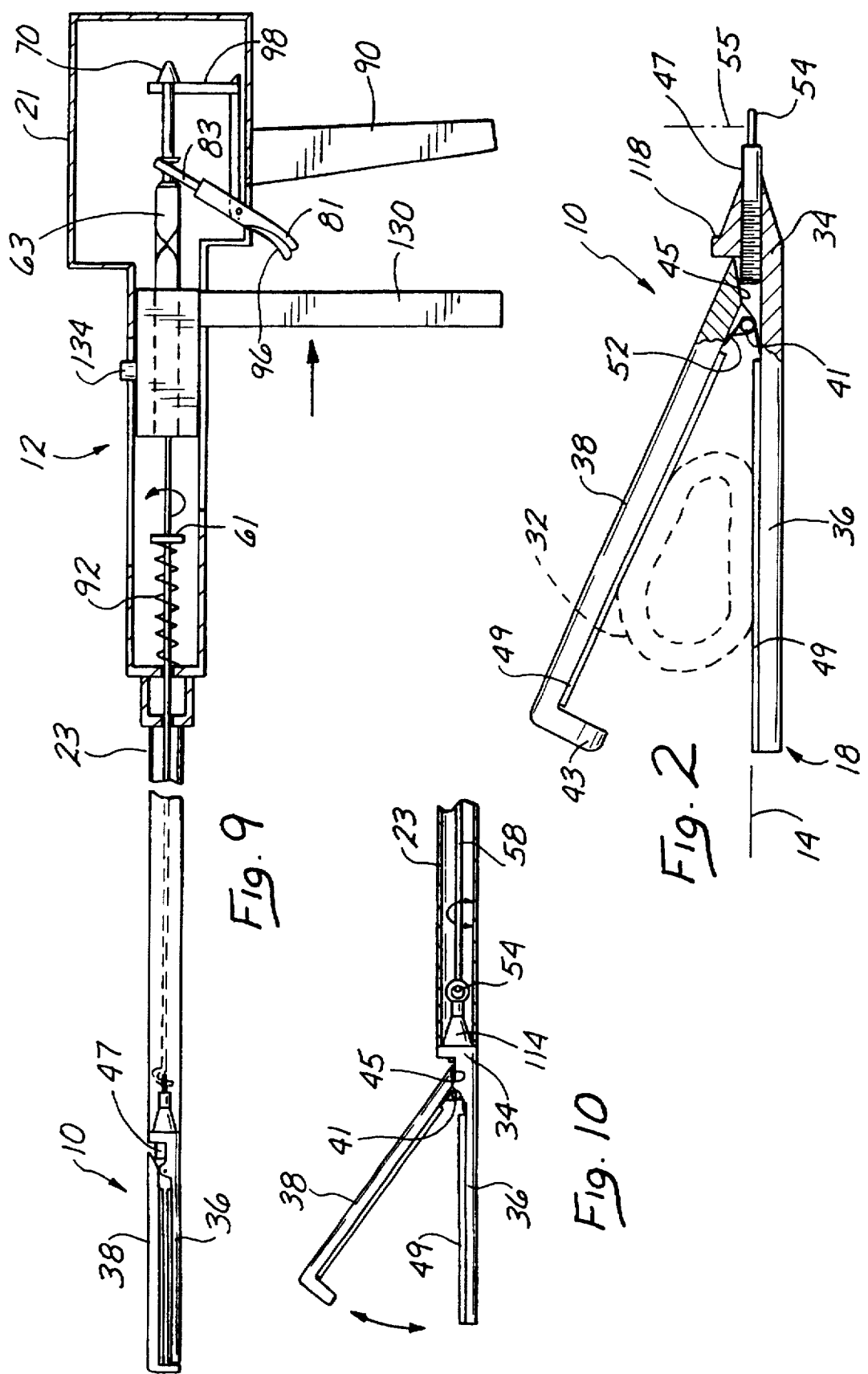

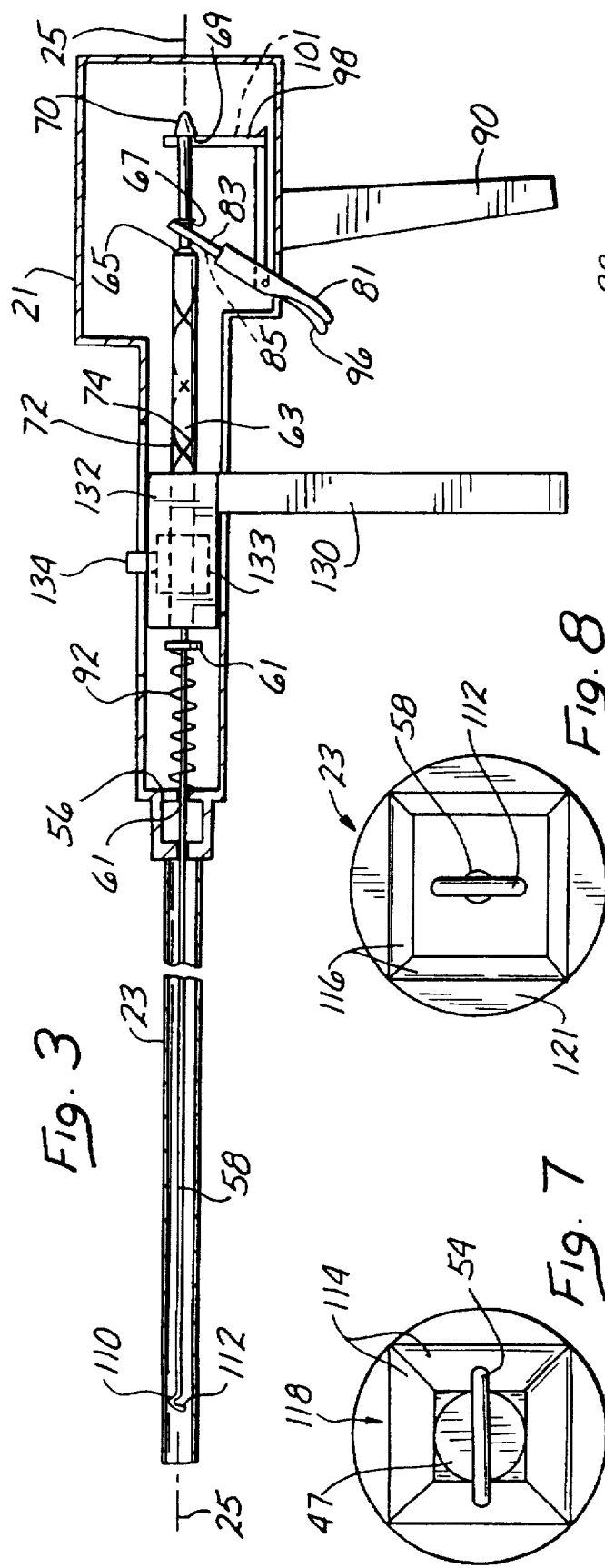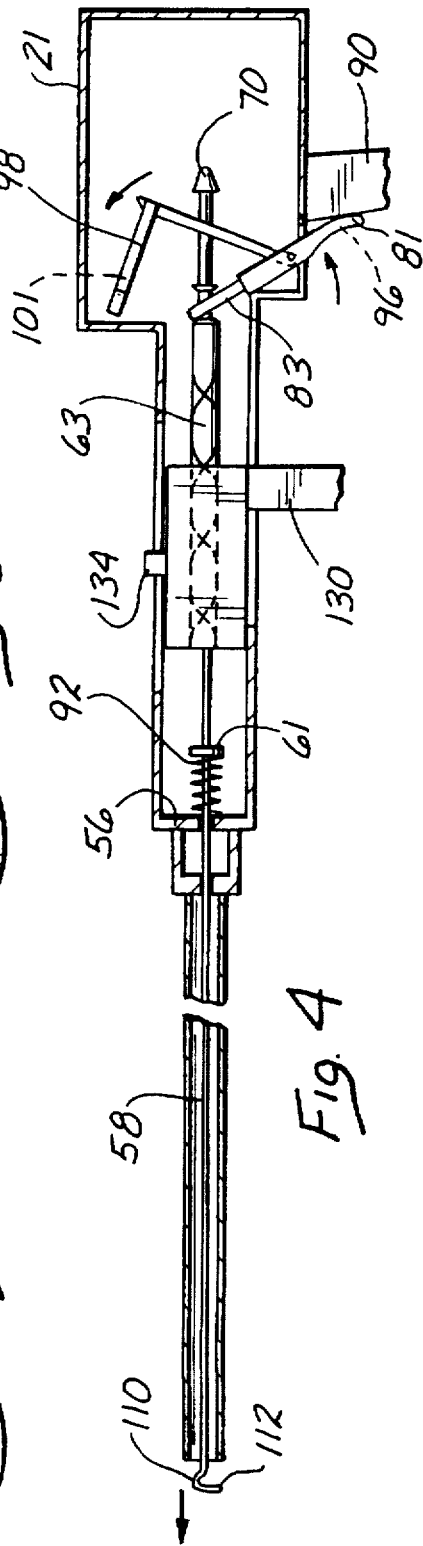

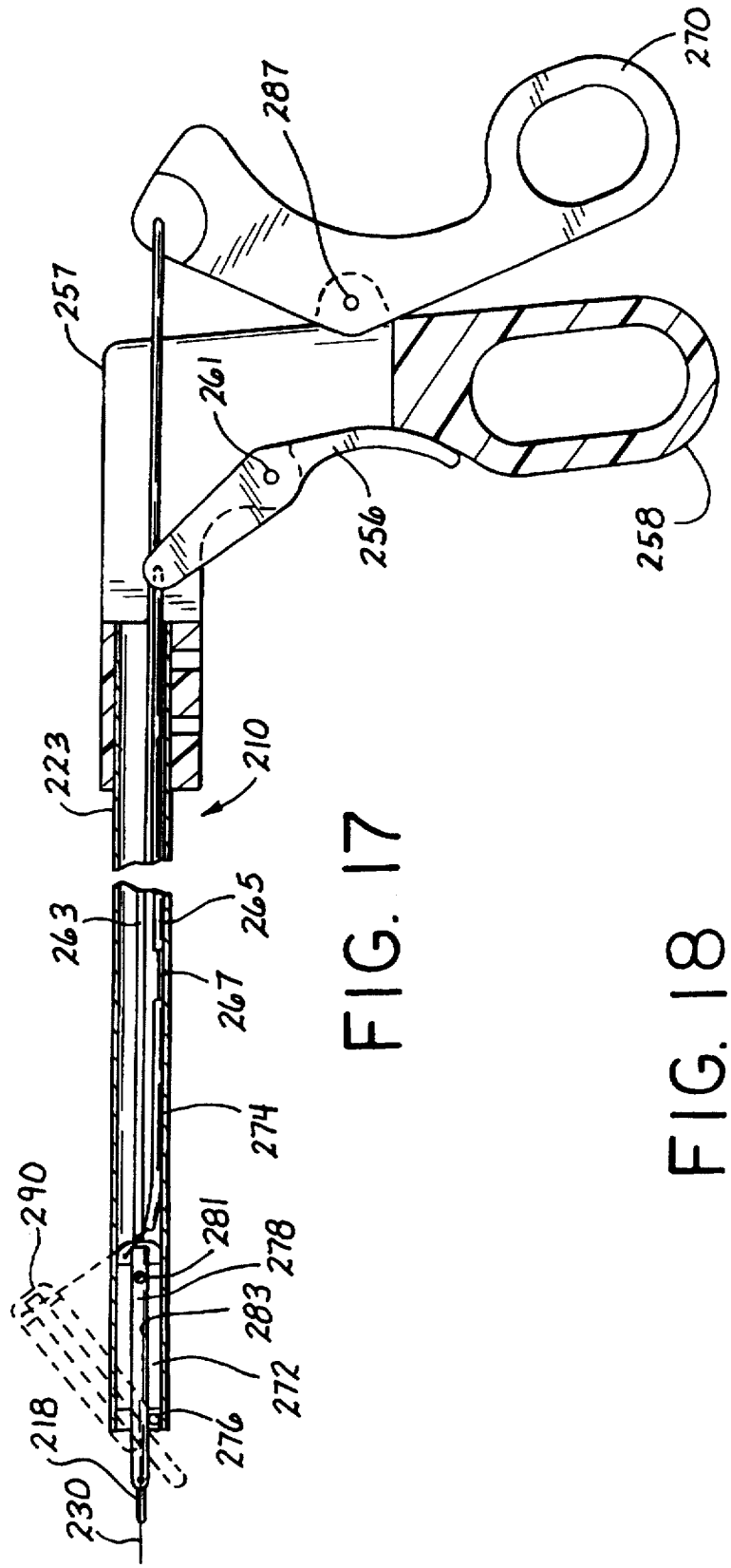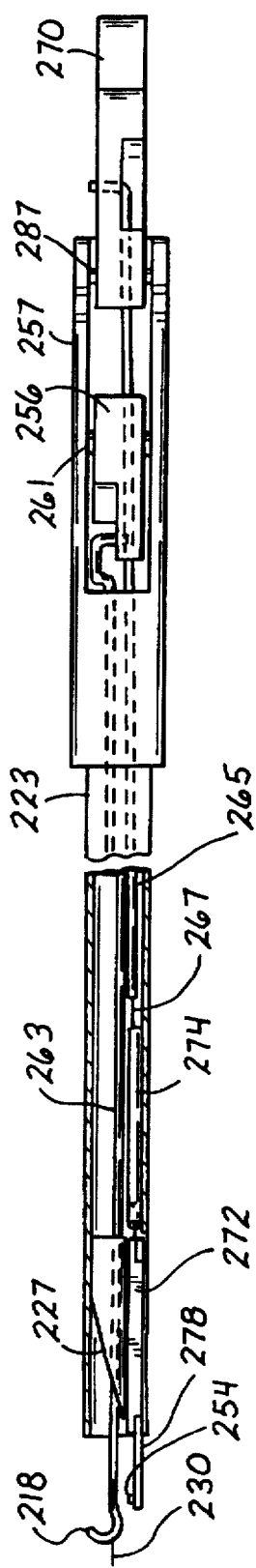

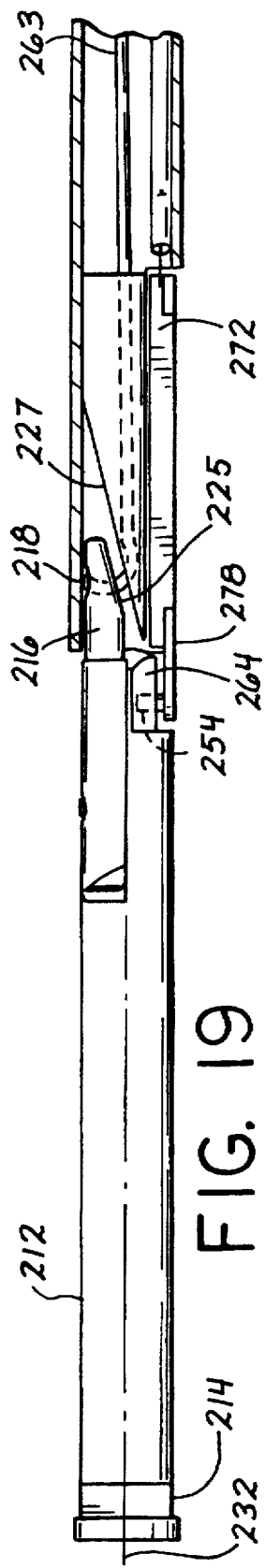

LAPAROSCOPIC SURGICAL CLAMP

CROSS REFERENCE TO RELATED APPLICATION

This application is a continuation-in-part of U.S. application Ser. No. 08/139,919 filed Oct. 20, 1993, now U.S. Pat. No. 5,496,333.

BACKGROUND OF THE INVENTION

1. Field of the Invention

This invention relates generally to surgical clamp apparatus and more specifically to clamps and clamp appliers for use in occluding body conduits.

2. Description of Related Art

Alternatives to large incision, open surgery are becoming increasingly important where they can provide reduced trauma and an increased speed of healing. For the patient, this ultimately equates to less time in the hospital which adds the economic advantage to these procedures.

Surgeries in the abdominal area are now being undertaken with a technique commonly referred to as laparoscopic surgery. In this procedure, access devices are used to puncture the abdominal wall or lapra and to provide working channels for instruments to perform the surgery. These access devices, commonly referred to as trocars, require relatively small incisions and provide working channels in a range of diameters between, for example, 5 mm and 21 mm.

Typical of these access devices is the trocar disclosed and claimed in applicant's patent U.S. Pat. No. 5,209,737 issued on May 11, 1993 which is incorporated herein by reference.

Since the objectives of the open surgeries and laparoscopic surgeries are often the same, it is not surprising that the occluding of body conduits is still of interest. However in the case of laparoscopic surgeries, this can be accomplished only with considerable difficulty due to the limited access provided by the trocars. Also, the confined abdominal cavity associated with laparoscopic surgeries generally requires additional retraction of organs in order to provide an enlarged surgical field.

Surgical clamps of the past have been adapted for open surgery wherein the size of the clamp is not constrained by the inside diameter of a trocar. These clamps commonly include long legs which form the jaws of the clamp and opposing smaller arms which are pivotal with the legs on a fulcrum disposed therebetween. These clamps are typically operable by a clamp applier which has a scissor configuration. The scissors of the applier in an open state engage the arms of the clamp and compress those arms to open the legs of the clamp. Unfortunately, with this configuration, either the long legs of the clamp are spread or the scissors are spread. In either case, this combination is not adapted for use with the narrow diameters offered by laparoscopic trocars.

The engagement mechanisms associated with these clamp systems of the prior art are also inappropriate for laparoscopic surgery. In the past, the clamp applier loosely engaged the clamp; this presented no problem to open surgery where one could merely reach into the cavity and retrieve a loose clamp. However, in laparoscopic surgery, the relatively closed surgical environment cannot tolerate this possibility of undesirable separation of the clamp from the applier.

SUMMARY OF THE INVENTION

These disadvantages of the prior art are overcome with the present invention which includes a novel surgical clamp and associated clamp applier both of which are insertable through a trocar. The clamp is provided with an elongate cylindrical configuration having an axis extending between the proximal end and a distal end. The clamp has two jaws which are relatively movable between an open state and a closed state. The first jaw may be formed as an extension of a supporting structure at the proximal end of the clamp, while the second jaw is pivotal on either the supporting structure or the first jaw. The first jaw has a first fixed set of teeth located near a proximal end of the first jaw, and the second jaw has a second fixed set of teeth located near a proximal end of the second jaw. A slot is formed within the first jaw for accommodating an external pin. The slot in the first jaw forms a flexible arm at a proximal end of the first jaw, and the first fixed set of teeth is located on this flexible arm. The first fixed set of teeth and the second fixed set of teeth are normally meshed together to prevent movement of the two jaws in a given direction. Application of a force by the pin on the flexible arm, however, disengages the first fixed set of teeth from the second fixed set of teeth, and thereby allows for movement of the first and second jaws in the given direction.

The clamp applier includes a housing and an elongate tube which is sized and configured to move through the trocar. The clamp applier also includes an engagement mechanism having a hook which can be advanced to engage the annulus of the clamp. Retraction of the engagement mechanism moves the clamp into a rigid operative position on the applier. Biasing means and locking means cooperate to retain the clamp in the operative position. In this operative position the engagement mechanism can be moved along a line, which is substantially perpendicular to an axis of the elongated tube, to thereby engage and disengage the first and the second fixed set of teeth of the surgical clamp.

In one aspect of the invention, a surgical clamp has first and second opposed jaws movable between an open position and a closed position. A ratchet wheel and pawl assembly is connected to the two jaws, and is adapted for allowing relative rotational movement of the two jaws in a first direction, while preventing relative rotational movement of the two jaws in a second direction. Movement of the two jaws in the second direction is accomplished by disengaging the pawl from the ratchet wheel. This disengagement function is performed by the engagement mechanism of the applier. A pin, which is connected to the distal end of the engagement mechanism, is movable along a line approximately perpendicular to the axis of the tube. Movement of the pin in an upward direction results in the ratchet wheel and pawl sliding upon one another, and movement of the pin in a downward direction results in disengagement of the pawl from the ratchet wheel. Additionally, movement of the pin in the upward direction applies a force to the upper jaw to thereby move a distal end of the upper jaw toward a distal end of the lower jaw. Movement of the pin in a downward direction, on the other hand, applies a force on the upper jaw, which moves the distal end of the upper jaw away from the distal end of the lower jaw. This open state allows the surgical clamp to accept a body conduit.

In another aspect of the invention, a surgical clamp has a longitudinal axis extending between a proximal end and a distal end, and includes a supporting structure. A pair of jaws is coupled to the supporting structure, and is movable between an open position and a closed position. A moving apparatus carried by the supporting structure is operable from near the proximal end of the clamp to move the jaws between the open position and the closed position. The moving apparatus includes a ratchet wheel and a pawl assembly that can be selectively engaged and disengaged to facilitate movement of the pair of jaws between the open position and the closed position. The surgical clamp combination further includes a clamp applier having a longitudinal axis extending between a proximal end and a distal end, and a tube disposed at the distal end of the clamp applier. An engaging apparatus is disposed within the tube for engaging the moving apparatus at the proximal end of the clamp. The engaging means is adapted to both selectively engage and disengage the ratchet wheel and pawl assembly, and is also adapted to apply forces on the surgical clamp to facilitate movement of the pair of jaws between the open position and the closed position. An operating apparatus is disposed at the proximal end of the clamp applier for operating the engaging apparatus to move the jaws of the clamp.

In another aspect of the invention, a clamp applier for selectively engaging a surgical clamp and for moving the surgical clamp between an open position and a closed position has an axis extending between a proximal end and a distal end of the clamp applier. The clamp applier includes a housing disposed at the proximal end, and a tube extending distally of the housing and configured to receive the surgical clamp. An engaging apparatus is disposed within the tube and is adapted for releasably engaging the surgical clamp. A first moving apparatus is disposed near the proximal end, and is connected to the engaging apparatus. The first moving apparatus is adapted for moving the engaging apparatus between an extended position where the engaging apparatus can engage the surgical clamp, and a retracted position where the surgical clamp is releasably held in contact with the clamp applier. An operating apparatus is disposed within the tube, as well, and is adapted for releasably engaging the surgical clamp. The operating apparatus is movable in two directions along a line that is approximately perpendicular to the axis of the clamp applier. Movement of the operating apparatus along the line results in movement of the surgical clamp between the open position and the closed position. A second moving apparatus is disposed in the proximal end of the clamp applier, and is connected to the operating apparatus. The second moving apparatus is adapted for moving the operating apparatus along the line that is approximately perpendicular to the axis.

The present invention, together with additional features and advantages thereof, may best be understood by reference to the following description taken in connection with the accompanying illustrative drawings.

BRIEF DESCRIPTION OF THE FIGURES

FIG. 1 is a perspective view of a clamp being applied by a clamp applier through a trocar to occlude a body conduit;

FIG. 2 is a axial cross-section view of one embodiment of the clamp illustrated in FIG. 1;

FIG. 3 is a axial cross-section view of one embodiment of the clamp applier illustrated in FIG. 1;

FIG. 4 is a axial cross-section view of the applier showing a rotatable shaft deployed to an extended position;

FIG. 5 is a radial cross-section view taken along lines 5—5 of FIG. 3;

FIG. 6 is a perspective view of the clamp aligned for engagement by the rotatable shaft of the clamp applier;

FIG. 7 is an elevation view of the proximal end of the clamp taken along lines 7—7 of FIG. 4;

FIG. 8 is an elevation view of the distal end of the clamp applier taken along lines 8—8 of FIG. 4;

FIG. 9 is a side view, partially in phantom, of the clamp operatively disposed on the clamp applier, and a handle operated to close the clamp;

FIG. 10 is a side view partially in phantom similar to FIG. 9 with the handle operated to open the jaws of the clamp;

FIG. 17 is a cross-sectional view of the clamp applier according to a second preferred embodiment of the present invention;

FIG. 18 is a top cross-sectional view of the clamp applier of the second preferred embodiment of the present invention;

FIG. 19 is a top cross-sectional view of both the surgical clamp and the clamp applier of the second preferred embodiment of the present invention;

FIG. 20 is a side cross-sectional view of the surgical clamp and the clamp applier of the second preferred embodiment of the present invention;

FIG. 21 is a cross-sectional view taken along line 21—21 of FIG. 20; and

FIG. 22 is a side view of the pivoting arm and actuator spring of the clamp applier of the second embodiment of the present invention.

DETAILED DESCRIPTION OF THE PREFERRED EMBODIMENTS

Figure 11:
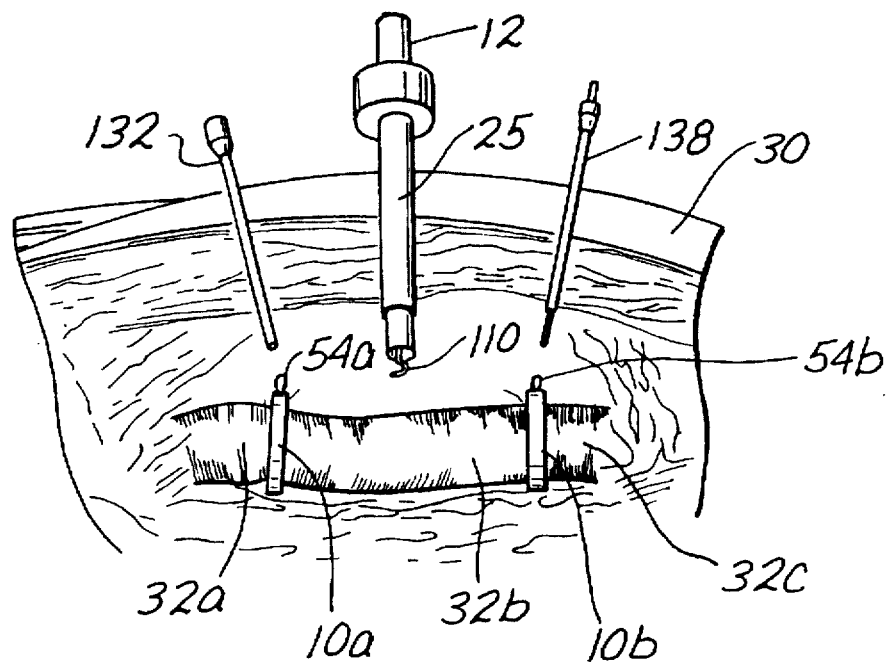
FIG. 11 is a perspective view of the abdominal cavity illustrating the placement of outer clamps in a bowelectomy procedure.

A surgical clamp and clamp applier are illustrated in FIG. 1 and designated respectively by the reference numerals 10 and 12. The clamp 10 has a generally cylindrical configuration with an axis 14 extending between a proximal end 16 and a distal end 18.

The clamp applier 12 includes a housing 21 and a tube 23 which extends distally of the housing 21 along an axis 25. The tube 23 and the clamp 10 are sized and configured to fit through a trocar 27 which has been positioned to provide access across the lapra or abdominal wall 30. Both the trocar 27 and the laparoscopic surgical procedure are described in greater detail in applicant's U.S. Pat. No. 5,209,737 issued on May 11, 1993 and entitled Lever Actuated Septum Seal.

Within the abdominal cavity, the clamp applier can be operated to open and close the clamp 10 about a body conduit, such as a bowel 32. Once the clamp 10 is attached to the bowel 32 it can function not only to occlude but also to cooperate with a retractor to move the bowel to a new location within the abdominal cavity.

In FIG. 2, the clamp 10 is illustrated in an axial cross-section view to include a supporting structure 34 and a pair of jaws 36 and 38. In the illustrated embodiment, the jaw 36 is formed as an extension of the supporting structure 34, while the jaw 38 is pivotal on the jaw 36 at a hinge 41.

The jaws 36 and 38 extend longitudinally toward the distal end 18 of the clamp 10 where one of the jaws, such as the jaw 38 is provided with an overhang 43. As the jaw 38 moves into proximity with the jaw 36, the overhang 43 encloses the bowel 32 prior to complete occlusion. This insures that the bowel 32 is captured between the jaws 36, 38 as the final occluding pressure is applied.

At the proximal end of the jaw 38, distally of the supporting structure 34, the jaw 38 is provided with a beveled surface 45 which faces inwardly toward the axis 14 of the clamp 10. This surface 45 functions in a camming action with a screw 47 which is rotatable within the supporting structure 34. In the preferred embodiment, the screw 47 is disposed for movement along the axis 14 of the clamp 10. As the screw 47 is rotated it moves axially through the supporting structure 34 to engage the beveled surface 45. Further axial movement of the screw 47 forces the jaw 38 to pivot on the hinge 41. This pivotal movement moves the jaw 38 from an open state illustrated in FIG. 2, wherein the jaw 38 is spaced from the jaw 36, to a closed state illustrated in FIG. 1 wherein the jaw 38 is brought into proximity with the jaw 36. In the closed state, the body conduit, such as the bowel 32, which is disposed between the jaws 36 and 38, is at least partially occluded. Soft inserts 49 can be provided along the jaws 36 and 38 to reduce trauma to the bowel 32.

A spring 52 can be provided in the hinge 41 in order to bias the jaws 36 and 38 to the open position. When the screw 47 is retracted, the jaw 38 will automatically separate from the jaw 36. When the screw 47 is advanced, the jaw 38 moves toward the jaw 36 against the bias of the spring 52. In an alternative embodiment (not shown), both of the jaws 36 and 38 are pivotal along the supporting structure 34 and include bevel surfaces, such as surface 45, which are engagable by the screw 47 to open and close the jaws 36, 38.

At the proximal end of the screw 47, an annulus 54 can be provided in order to facilitate attachment to the clamp applier 12. The annulus 54 preferably has an axis 55 which perpendicularly intersects the axis 14 of the clamp 10.

The clamp applier 12 is illustrated in the axial cross-section view of FIG. 3 which shows the interior regions of the housing 21 and the tube 23. The tube 23 is attached to the distal end of the housing 21 where a distal wall 56 extends generally perpendicular to the axis 25.

A shaft 58 extends through the tube 23 and proximally through a hole 61 in the distal wall 56 into the housing 21. Within the housing 21, the shaft 58 extends through a wafer 62 and terminates in the distal end of an aladdin screw 63. At its proximal end, the diameter of the aladdin screw 63 is decreased to define a proximal facing shoulder 65, increased to define a distally facing shoulder 67, and enlarged again at a distally facing shoulder 69 formed on a terminal lug 70. The aladdin screw 63 has an outer cylindrical surface which is provided with counter-rotating spiral grooves 72 and 74.

A trigger 81 pivotal on the housing 21 operates a pair of fingers 83 and 85. These fingers are closely spaced to receive the reduced diameter of the aladdin screw 63 between the shoulders 65 and 67. A handle 90 fixed to the housing 21 provides support, in the palm of a user's hand (not shown), against which the trigger 81 can be operated. Pulling the trigger causes the fingers 83, 85 to engage the proximally facing shoulder 65 and to move the aladdin screw 63 and associated shaft 58 distally as illustrated in FIG. 4.

With the wafer 62 fixed to the shaft 58 and the wall 56 fixed to the housing 21, a compression spring 92 disposed therebetween around the shaft 58 functions to bias the aladdin screw 63 and shaft 58 toward a proximal retracted position. This proximal position is illustrated in FIG. 3 along with a locking mechanism which functions to maintain the screw 63 and the shaft 58 in the proximal position. The locking mechanism includes a second trigger 96 and a pair of fingers 98 and 101 which engage the aladdin screw between the shoulders 67 and 69. In a preferred embodiment, these fingers 98, 101 extend perpendicular to the axis 25 and abut the distally facing shoulder 69 to hold the terminal lug 70 in a locked proximal position. When the trigger 96 is in a distal position, spaced from the handle 90, the aladdin screw 63 and shaft 58 are locked in the proximal position. When the trigger 96 is pulled against the handle 90 as illustrated in FIG. 4, the fingers 98 and 101 are removed from the terminal lug 70 to permit distal movement of the screw 63 and shaft 58. When both of the triggers 81 and 96 are moved against the handle 90, the trigger 96 initially releases the lock as the trigger 81 deploys the screw 93 and shaft 58 to the distal extended position.

The proximal and distal positions of the shaft 58 are best described with reference to the distal end of the shaft 58 which is formed in the shape of a hook 110. In a preferred embodiment, the distal end of the hook 110 includes a terminal portion 112 which extends generally perpendicular to the axis 25. The hook 110 is sized and configured to engage the annulus 54 at the proximal end of the clamp 10. Thus the hook 110 and shaft 58 function as an engagement mechanism for initially engaging the clamp 10 and ultimately moving the clamp into operative disposition relative to the tube 23.

The trigger 81 functions to deploy this engaging mechanism to the distal position wherein the hook 110 extends beyond the end of the tube 23. In this position the terminal end 112 of the hook 110 is accessible for insertion into the annulus 54. In FIG. 6, the clamp 10 is illustrated in a free state wherein it is not attached to the clamp applier 12. Once the hook 110 engages the annulus 54 and the trigger 81 is released, however, the spring 92 functions to move the shaft 58 and hook 110 to the proximal position drawing the annulus 54 of the clamp 10 into the tube 23. In a preferred embodiment, this brings the clamp 10 into abutting relationship with the distal end of the tube 23 wherein the axes 14 and 25 are aligned to facilitate insertion through the trocar 27.

It will be apparent that the clamp 10 can be otherwise engaged by the shaft 58 of the applier 12 in a locking but operative position. In general, the screw 47 needs to be positively engaged by the shaft 58 so that the clamp 10 cannot be accidentally dropped into the abdominal cavity. This positive engagement between the clamp 10 and shaft 58 must also be capable of transmitting the rotational movement of the shaft 58 to the screw 47.

In this operative position, the supporting structure 34 of the clamp 10 can be held against axial movement by the locking mechanism including the trigger 96. The supporting structure of the clamp 10 is held against rotational movement relative to the tube 23 by a key 114 on the supporting structure 34 and associated key way 116 on the tube 23. In a preferred embodiment, the key 114 is formed with four sides which are equally spaced around and inclined proximally toward the axis 14. This key 114 registers with similar surfaces which are formed on the inside of the tube 23 and define the key way 116. At the base of the key 114, the supporting structure 34 forms a proximally facing shoulder 118, best illustrated in FIG. 2. This shoulder 118 is adapted to register with a distal surface 121 on the tube 23. Other configurations for the key 114 and key way 116 will be apparent. In general, it is desirable that the key 114 can be tapered inwardly, proximally in order to achieve axial alignment of the clamp 10 and tube 23. Any noncircular shape for the key 114 and key way 116 would appear to inhibit rotational movement between the clamp 10 and tube 23.

When the clamp 10 is operatively disposed, the annulus 54 is engaged by the hook 110 interiorly of the tube 23. The key 114 registers with the key way 116, and the shoulder 118 is in abutting relationship with the surface 121. With the proximal bias on the shaft 58, the clamp 10 is automatically moved to this operative position where it can be locked in place by operation of the trigger 96.

Once the clamp 10 is operatively disposed at the distal end of the clamp applier 12, it will normally be desirable to operate the screw 47 in order to open and close the jaw 38. This rotation of the screw 47 is accomplished in a preferred embodiment by rotating the shaft 58. For example, as illustrated in FIG. 3, a second handle 130 can be provided on the housing 21 for engagement by the fingers of a user's hand. This handle is fixed to a follower block 132 which is movable along the housing 21 in cooperation with the aladdin screw 63. This follower block 132 includes a follower 133 movable between two positions by operation of a tab 134 which is accessible outside the housing 21.

In accordance with the normal operation of an aladdin screw, the tab 134 is operable to bring the follower 133 into registration with one of the grooves 72 and 74. When the follower 133 engages the groove 74 for example, movement of the handle 130 toward the handle 90 causes the aladdin screw 63 to rotate in a clockwise direction. This causes the shaft 58 to rotate in a clockwise direction and to advance the screw 47 of the clamp 10 toward the beveled surface 45. When the tab 134 is operated to move the follower into engagement with the groove 72, movement of the handle 130 toward the handle 90 rotates the aladdin screw 63 in a counter-clockwise direction. This causes the shaft 58 to move counter-clockwise and the screw 47 to be withdrawn from the beveled surface 45 permitting the jaws 36, 38 to open.

Thus the aladdin screw 63 and associated follower 133, tab 134 and handle 130 function so that the linear movement of the handle 130 is converted into rotational movement of the shaft 58. In this particular embodiment, movement of the handle 130 in a single direction, toward the handle 90, can produce either clockwise or counter-clockwise rotation of the shaft 58 depending on the position of the tab 134 and associated follower 133.

In a preferred method associated with the invention, the clamp 10 is initially in a free state, unattached to the clamp applier 12. In order to prepare the applier 12 to receive the clamp 10, the shaft 58 initially must be unlocked. This requires that the trigger 96 be pulled against the handle 20 in order to remove the fingers 98, 101 from the shoulder 69 of the terminal lug 70. Thus operation of the trigger 96 elevates the fingers 98, 101 as illustrated in FIG. 4, to free the shaft 58 for axial movement along the axis 25.

In this unlocked state, the shaft 58 is biased in the retracted position so that operation of the trigger 81 is required to deploy the hook 110. By pulling the trigger 81 against the handle 90, the fingers 83, 85 are brought into engagement with the shoulder 65. Further proximal movement of the trigger 81 moves the aladdin screw 63 and shaft 58 against the bias of the spring 92 to the extended position illustrated in FIG. 4.

In this extended position, the terminal end 112 of the hook 110 can be introduced through the annulus 54 to engage the clamp 10. When the trigger 81 is released, the bias of the spring 92 moves the shaft and aladdin screw 63 toward the retracted position. The hook 110 is drawn into the tube 23 along with the annulus 54, and the key 114 on the clamp 10 registers with the key way 116 at the distal end of the tube 23. When the shoulders 118 abut the distal surface 121, the clamp 10 has achieved its operative position. It can be retained in this position by moving the trigger 96 distally so that the fingers 98, 101, engage the shoulder 69 on the terminal lug 70.

In this operative position, registration of the key 114 and key way 116 seeks to align the axis 14 of the clamp 10 with the axis 25 of the clamp applier 12. Axial movement of the clamp 10 relative to the applier 12 is inhibited by the locking mechanism, while rotational movement of the clamp 10 relative to the applier 12 is inhibited by the registration of the key 114 and key way 116. In this operative position, the shaft 56 can be rotated in two directions to either open or close the jaws 36, 38.

In an embodiment including the aladdin screw 63, operation of the handle 130 in a single direction, for example toward the handle 90, can cause rotation of the shaft 58 in either of the two directions. For example, if the tab 134 is positioned so that the follower 133 engages the groove 74, movement of the handle 130 toward the handle 90 will be converted into clockwise rotation of the shaft 58. This will cause the screw 47 to advance into the beveled surface 45 causing the jaws 36 and 38 as illustrated in FIG. 9. Alternatively, with the tab 134 disposed in the opposite position, the follower 133 engages the groove 72 of the aladdin screw 63. Then, movement of the handle 130 toward the handle 90 can be converted into rotational movement of the shaft 58 in the counter-clockwise direction. This will remove the screw 47 from the beveled surface 45 resulting in separation of the jaws 36, 38 by operation of the spring 52, as illustrated in FIG. 10.

While the aladdin screw 63 is incorporated in a preferred embodiment, it will be apparent that a single screw could also be used. In such an embodiment, operation of the handle 130 toward the handle 90 could result in the clockwise rotation of the shaft 58 while movement of the handle 130 away from the handle 90 would result in counter-clockwise rotation of the shaft 58.

The foregoing apparatus and method are of particular interest in a surgical procedure providing for removal of a section of the bowel 32. This procedure is illustrated in FIGS. 11–14 wherein three sections of the bowel are designated consecutively by the reference numerals 32a, 32b and 32c. In this procedure, it is the center section 32b which is to be removed.

Initially a clamp 10a is engaged by the clamp applier 12 and inserted through the trocar 25 to operatively occlude the bowel between the section 32a and 32b. After the clamp 10a has been operatively positioned, the applier 12 can be operated to disengage the hook 110 from the associated annulus 54a. Then a second clamp 10b is operatively disposed to occlude the bowel between the section 32b and the section 32c. After the clamp 10b has been positioned, the clamp applier 12 can be operated to release the hook 110 from the associated annulus 54b.

Figure 12:
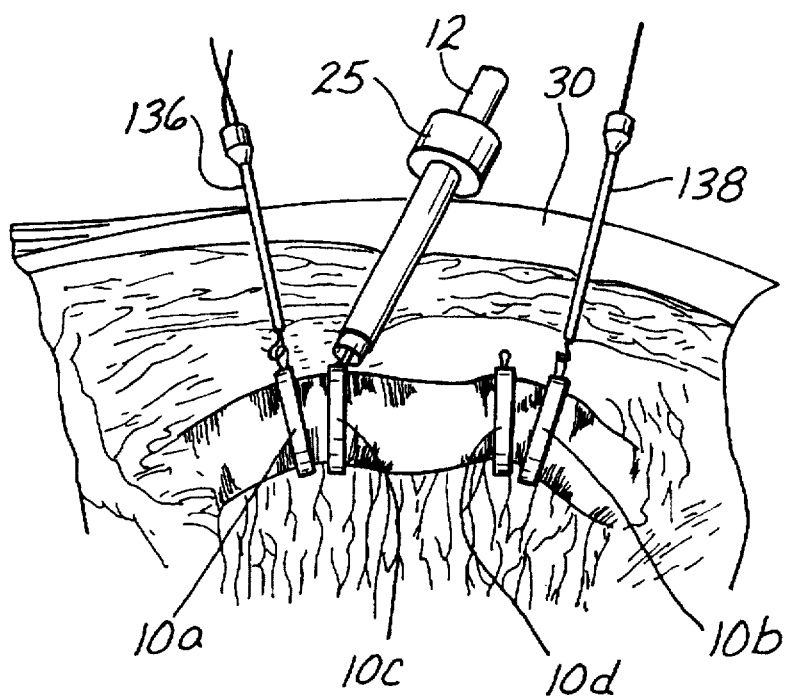
FIG. 12 is a perspective view similar to FIG. 11 showing the placement of inner clamps in the procedure.

At this point it may be desirable to elevate the bowel 32 in order to provide better access within the abdominal cavity. For this purpose, retractors 136 and 138 can be introduced through the abdominal wall 30 to engage the respective annulus 54a and 54b. Alternatively, the retractors 136, 138 can be introduced through secondary trocars (not shown) similar to the trocar 25. Once the clamps 10a and 10b have been engaged by the respective retractors 136, 138, they can be moved toward the abdominal wall 30 to elevate the bowel 32 as illustrated in FIG. 12.

In this elevated location, two additional clamps 10c and 10d can be attached to occlude the bowel 32 adjacent the respective clamps 10a and 10b. These clamps 10c and 10d can also be released and the clamp applier 12 removed from the trocar 25.

Figure 13:
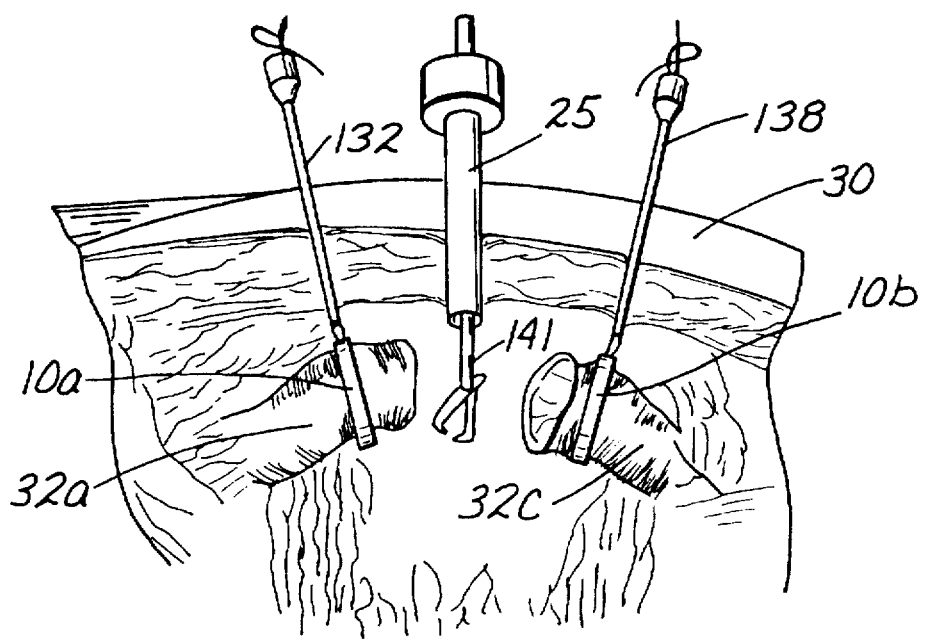
FIG. 13 is a perspective view similar to FIG. 11 illustrating the removal of a bowel section from the abdominal cavity.
Figure 14:
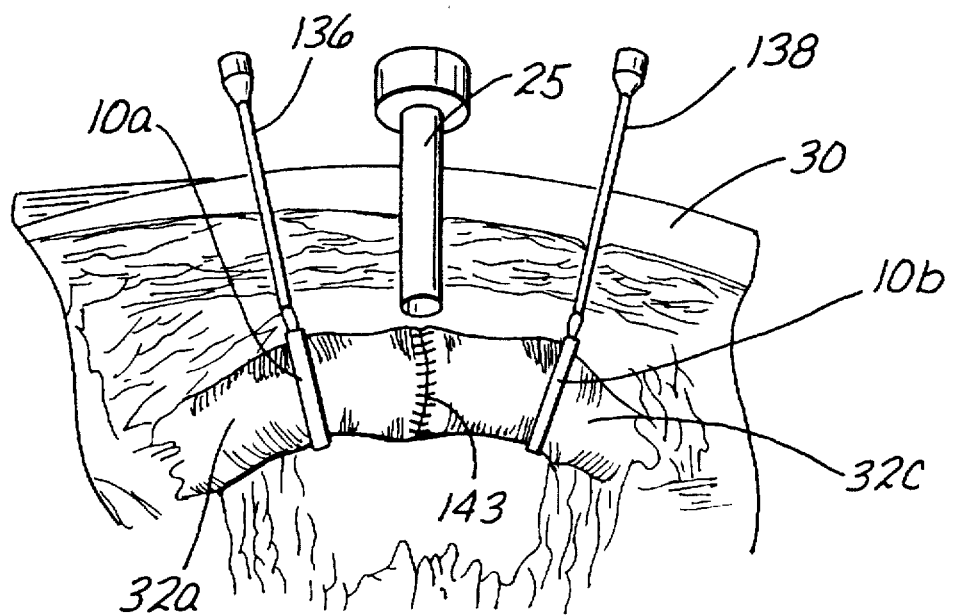
FIG. 14 is a perspective view similar to FIG. 11 illustrating the suturing of the bowel following removal of the bowel section.

With the clamps 10a–10d appropriately positioned, the center section 32b of the bowel 32 can be severed from the sections 32a and 32c by appropriate incisions between the clamp pairs 10a, 10c and 10d, 10b. At this point, the clamp applier 12 can be reinserted through the trocar 25 to engage the clamps 10c and 10d and to remove these clamps through the trocar 25. A grasper 141 may also be inserted to withdraw the central section 32b of the bowel, as illustrated in FIG. 13. Finally, a suturing mechanism (not shown) can be introduced through the trocar 12 to facilitate the placement of sutures 143 between the bowel portion 32a to the bowel portion 32c.

At the completion of this step, the retractors 136, 138 can be operated to disengage the clamps 10a, 10b, and the clamp applier 12 can be reintroduced to retrieve the clamps 10a, 10b. Ultimately the retractors 136, 138 and the trocar 25 are removed from the abdominal wall 30 to complete the procedure.

Figure 15:
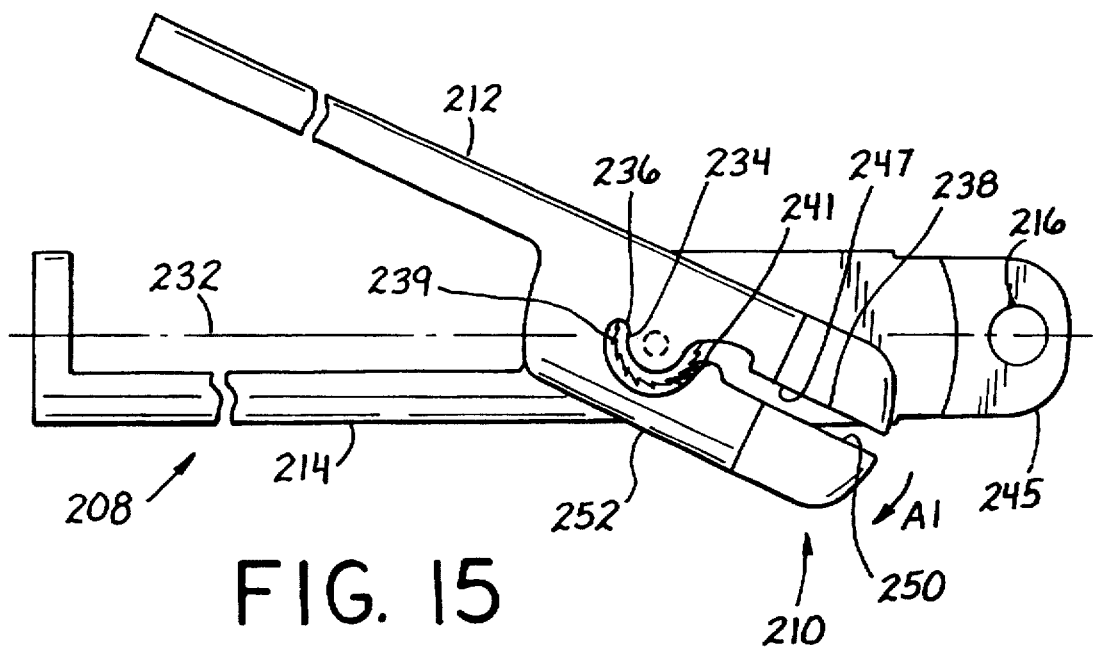
FIG. 15 is a perspective view of a second embodiment of the surgical clamp.

A second preferred embodiment of the clamp is illustrated in FIG. 15. The surgical clamp 208 comprises a first jaw 212 and a second jaw 214. The first jaw 212 and the second jaw 214 preferably comprise injection molded plastic. The surgical clamp 208 comprises a proximal end near an annulus 216, a distal end opposite the annulus 216, and an axis 230 extending between the proximal end and the distal end. Similarly to the embodiment of the clamp 10 described above with reference to FIG. 2, the surgical clamp 208 comprises the annulus 216 for accommodating a hook 218 (FIG. 17). The hook 218 pulls the proximal portion 221 of the surgical clamp 208 into contact with a tube 223 (FIG. 17), which preferably comprises stainless steel and is similar to the tube 23 shown in FIG. 1, for example. A wedge 225 of the surgical clamp 208 moves into contact with an incline 227 (FIG. 17), which is disposed within the tube 223. The close fit between the wedge 225 and the incline 227 serves to align an axis 230 (FIG. 17) of the tube 223 with a clamp axis 232 and, further, prevents the surgical clamp 208 from rotating about either of these axes 230 and 232.

The first jaw 212 comprises a slot 234, which includes a curved portion 236 and a straight portion 238. The slot 234 is preferably integrally formed into the first jaw 212. A fixed ratchet wheel 239, which is preferably integrally molded with the second jaw 214, can be seen through the curved portion 236 of the slot 234. A fixed pawl 243, which is preferably integrally molded with the first jaw 212, can also be seen through the curved portion 236 of the slot 234.

Figure 16:
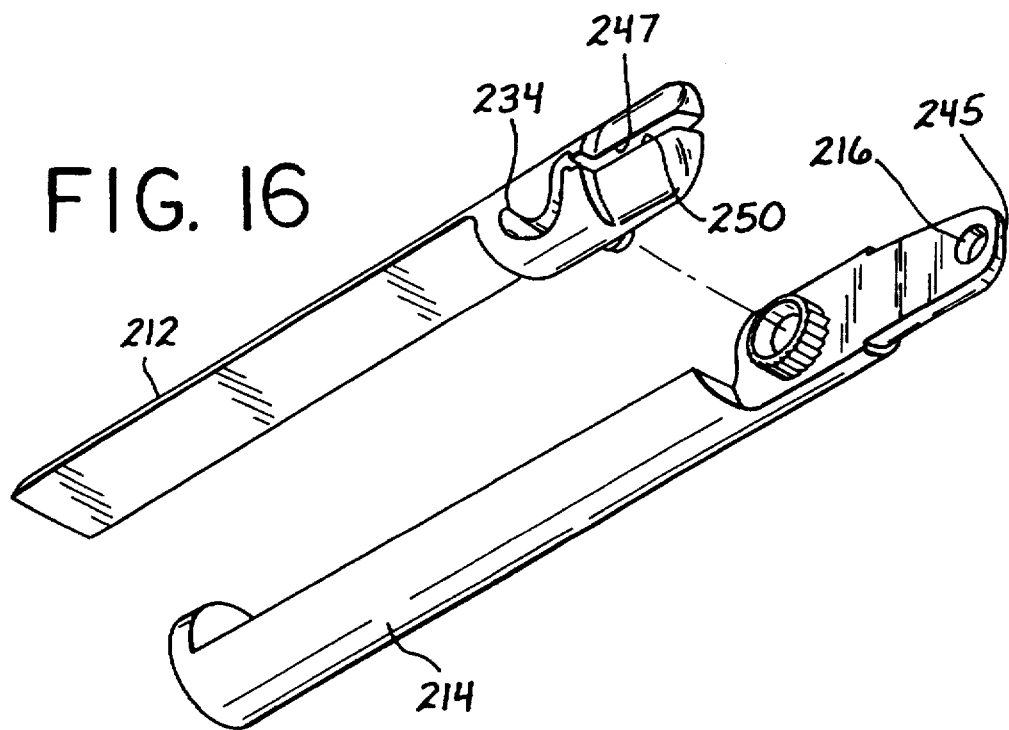
FIG. 16 is an exploded view of the surgical clamp of the second preferred embodiment.

FIG. 16 shows the first jaw 212 disassembled from the second jaw 214. The first jaw 212 is pivotally held to the second jaw 214 with a snap protrusion 240 of the first jaw 212 that fits into a snap aperture 242 of the second jaw 214. As can be best seen with reference to FIG. 16, the teeth of the fixed ratchet wheel 239 are slanted in a counter-clockwise direction. The fixed pawl 243 of the first jaw 212 are also slanted in a counter-clockwise direction. This orientation of the teeth of the fixed ratchet wheel 239 and of the fixed pawl 243 allows the two sets of teeth 239 and 243 to slide upon one another as the first jaw 212 is moved toward the second jaw 214, but does not allow the two sets of teeth 239 and 243 to slide upon one another as the first jaw 212 is moved away from the second jaw 214. Thus, this slanting of the teeth 239 and 243 allows the two jaws 212 and 214 to be shut, but will does not allow the two jaws 212 and 214 to be opened.

If a force as applied to the end 245 of the first jaw 212 in the direction of the arrow A1, however, then the end 245 tends to bend in the direction of the force, relative to the rest of the first jaw 212, to thereby release the fixed pawl 243 from contact with the teeth of the fixed ratchet wheel 239. Any force in the direction of the arrow A1 should be roughly perpendicular to a line formed by the straight portion 238 of the slot 234 and should be in a direction from the first side 247 to the second side 250. The curved portion 236 of the slot 234 provides for bending of the flexible area 252 of the second jaw 214, which results in movement of the end 245 in the direction of the applied force, to thereby disengage the fixed pawl 243 from the teeth of the fixed ratchet wheel 239. Although the slot 234 having a curved portion 236 and a straight portion 238 are presently preferred, other shapes and sizes of slots may be implemented, according to design parameters.

In the presently preferred embodiment, a pin 254 fits within the straight portion 238 of the slot 234. Movement of the pin 254 within the slot 234 in the direction of the arrow A1 results in the pin 254 contacting the second side 250. This application of force by the pin 254 onto the second side 250 results in disengagement of the teeth and, consequently, in movement of the first jaw 212 away from the second jaw 214. Movement of the pin within the slot 234 in a direction opposite to the arrow A1 results in the pin 254 contacting the first side 247. This application of force by the pin 254 onto the first side 247 results in engagement of the teeth, but the teeth slide upon one another and allow the first jaw 212 to be moved toward the second jaw 214. Thus, according to the present invention, movement of a single pin 254 within the slot 234 functions to open and close the surgical clamp 208.

FIG. 17 illustrates a clamp applier 210, which is used in conjunction with the surgical clamp 208. The clamp applier 210 comprises an axis 230, which extends between a proximal end of the clamp applier 210 near the movable handle 270 and a distal end of the clamp applier 210 near a pivoting arm 272. FIG. 18 illustrates a top view of the clamp applier 210. In operation, a user moves the trigger 256 in the proximal direction toward the stationary handle 258, which is preferably integrally molded with the housing 257. The trigger 256 rotates in a counter-clockwise direction about the first hinge 261, and causes the shaft 263 and the hook 218 to move forward in the distal direction.

The hook 218 is first inserted through the annulus 216 of the surgical clamp 208. Next, the user releases the trigger 256 which causes the spring-biased hook 218 to be retracted back into the tube 223. As the proximal end of the surgical clamp 208 is pulled into the tube 223, the wedge 225 of the surgical clamp 208 moves into contact with the incline 227.

The top view shown in FIG. 19 illustrates the registering of the wedge 225 of the surgical clamp 208 with the incline 227 of the clamp applier 210. The close fit between the wedge 225 and the incline 227 serves to align the axis 230 of the clamp applier 210 with the clamp axis 232 and, further, prevents the surgical clamp 208 from rotating about either of these axes 230 and 232. A side view of the surgical clamp 208 and the clamp applier 210 shown in FIG. 19 is shown in FIG. 20.

As the wedge 225 of the surgical clamp 208 is drawn into contact with the incline 227 of the clamp applier 210, the pin 254 of the clamp applier 210 is automatically positioned within the straight portion 238 of the slot 234. A cross section taken along the line 21, 21 of FIG. 20 is shown in FIG. 21. The pin 254 initially comes into contact with either the straight portion 238 of the slot 234, or comes into contact with one of the two ramps 264 disposed on opposite sides of the straight portion 238 of the slot 234. If the pin 254 initially contacts one of the two ramps 264, then further movement of the surgical clamp 208 by the hook 218 causes the pin 254 to travel up the ramp 264 and into the straight portion 238 of the slot 234. Since the actuator spring 278 is flexible in a direction normal to the channel 283 of the pivoting arm 271, as shown in FIG. 22, movement of the pin 254 up the ramp 264 does not break or damage the actuator spring 278.

A rod 265 connects a nitinol wire 267 to the movable handle 270. The stationary handle 258 and the movable handle 270 together comprise a set of scissor handles, which is easy to operate with a single hand of the user. The user can move the movable handle 270 toward and away from the stationary handle 258 with ease. The nitinol wire 267 is connected between the rod 265 and the pivoting arm 272. In the presently preferred embodiment, a stainless steel hypotube 274 surrounds the nitinol wire 267 between the rod 265 and the pivoting arm 272. The stainless steel hypotube 274 serves to guide the nitinol wire 267 as the nitinol wire 267 moves in forward and reverse directions within the stainless steel hypotube 274.

The pivoting arm 272, which is pivotal in a vertical plane about a pivot hinge 276, has an actuator spring 278 secured thereto. The actuator spring 278 is secured to the pivoting arm 272 with a single screw 281. In the presently preferred embodiment, the actuator spring 278 comprises a leaf spring, which fits into a channel 283 of the pivoting arm 272. The channel 283 of the pivoting arm 272 prevents the actuator spring 278 from moving in the vertical plane, except for when the pivoting arm 272 is also moved in the vertical plane. Since the actuator spring 278 is only secured to the channel 283 at the proximal end of the actuator spring 278, the actuator spring 278 is able to move slightly in a horizontal plane, which passes through the channel 283. Thus, the distal end of the actuator spring 278 is able to move away from the channel 283, but the proximal end of the actuator spring 278 is secured to the channel by the single screw 281. The positioning of the actuator spring 278, after movement away from the channel 285, is shown in phantom in FIG. 22 and denoted by the reference number 284. As the pivoting arm 272 is pivoted about the pivot hinge 276, the actuator spring 278 also pivots about the pivot hinge 276. The actuator spring 278 remains in or directly above the channel 283 of the pivoting arm 272 during this movement.

When the movable handle 270 is moved in the forward direction by counter-clockwise rotation of the movable handle 270 about the second hinge 287, the rod 265 is moved forward in the distal direction. Forward movement of the rod 265 results in forward movement of the nitinol wire 267 within the stainless steel hypotube 274. The forward movement of the nitinol wire 267 within the stainless steel hypotube 274 results in rotation of the pivoting arm 272 in the counter-clockwise direction about the pivot hinge 276. This rotation of the pivoting arm 272 causes the proximal portion of the pivoting arm 272, which is connected to the nitinol wire 267, to move upward and to issue through a slot in the tube 223. Alternatively, the tube 223 may be configured to surround only the incline 227 and the shaft 263, but not the pivoting arm 272 and the actuator spring 278. The positioning of the pivoting arm 272 and nitinol wire 267, after pivoting in the counter-clockwise direction, is shown in phantom in FIG. 17 and denoted by the reference number 290. In either case, the counter-clockwise movement about the pivot hinge 276 causes the pin 254 of the actuator spring 278 to move in a downward direction, resulting in movement of the first jaw 212 away from the second jaw 214.

When the movable handle 270 is moved in the reverse direction by clockwise rotation of the movable handle 270 about the second hinge 287, on the other hand, the rod 265 is moved in a reverse direction. Reverse movement of the rod 265 results in reverse movement of the nitinol wire 267 within the stainless steel hypotube 274. The reverse movement of the nitinol wire 267 within the stainless steel hypotube 274 results in rotation of the pivoting arm 272 in the clockwise direction about the pivot hinge 276, which causes the pin 254 of the actuator spring 278 to move in an upward direction. This upward movement of the pin 254 results in movement of the first jaw 212 toward the second jaw 214. The surgical clamp 208 and clamp applier 210 can be used similarly to the surgical clamp 10 and clamp applier 12, as discussed above with reference to FIGS. 11–14, for example.

In the foregoing discussion, several preferred embodiments, clamp applier, and associated method have been described. Many variations on this concept will now be apparent. For example, many clamp configurations can be adapted to provide a generally cylindrical configuration with as\ws openable and closeable by operation of a mechanism generally along the axis of the clamp, or by movement of a mechanism in a direction normal to the axis of the clamp. With these constraints, the clamp can be introduced through a trocar to facilitate a wide variation in laparoscopic procedures.

Both apparatus and methods for operating such a clamp with an appropriate clamp applier will also be apparent. Initially the applier must have an elongate configuration also sized and configured to fit through a trocar. An appropriate mechanism for holding the clamp in a fixed operable position will be desirable. Once the clamp is in this position, an appropriate mechanism will open and close the jaws of the clamp.

Given the wide variation in the possibilities for embodying these concepts, one is cautioned not to determine the scope of the invention merely with reference to the drawings and associated description, but rather with reference to the follow claims.

Although exemplary embodiments of the invention have been shown and described, many other changes, modifications and substitutions, in addition to those set forth in the above paragraph, may be made by one having ordinary skill in the art without necessarily departing from the spirit and scope of this invention.

We claim:

1. A surgical clamp, comprising:
    a first jaw having a proximal end and a distal end, the first jaw having a first fixed set of teeth located near the proximal end of the first jaw;
    a second jaw having a proximal end and a distal end, the second jaw having a second fixed set of teeth located near the proximal end of the second jaw;
    at least the first jaw being movable between a first position wherein the first set of teeth are spaced from the second set of teeth, and a second position wherein the first set of teeth mesh with the second set of teeth; and
    at least one of the first jaw and the second jaw being movable when the first jaw is in the second position, between an open state wherein the distal end of the first jaw is spaced from the distal end of the second jaw to accept a body conduit, and a closed state wherein the distal end of the first jaw is proximate to the distal end of the second jaw to at least partially occlude the body conduit.

2. The surgical clamp recited in claim 1, the first jaw being rotatably secured to the second jaw in proximity to the respective first set of teeth and the second fixed set of teeth, so that the first fixed set of teeth and the second fixed set of teeth can be moved between the first position and the second position.

3. A surgical clamp, comprising:

a first jaw having a proximal end and a distal end, the first jaw having a first fixed set of teeth located near the proximal end of the first jaw;

a second jaw having a proximal end and a distal end, the second jaw having a second fixed set of teeth located near the proximal end of the second jaw;

moving means for moving the first jaw and the second jaw between an open state wherein the distal end of the first jaw is spaced from the distal end of the second jaw to accept a body conduit, and a closed state wherein the distal end of the first jaw and the distal end of the second jaw are proximate to at least partially occlude the body conduit, the moving means being adaptable for moving the first fixed set of teeth in and out of mesh with the second fixed set of teeth;

the moving means being configured to receive a force from an external device, the force being sufficient to move the first jaw and the second jaw between the open state and the closed state;

the first jaw being rotatably secured to the second jaw near the respective first set of teeth and the second set of teeth, so that the first set of teeth and the second set of teeth can be moved in and out of mesh;

the moving means comprising a slot disposed within the first jaw near the proximal end of the first jaw; and the external device comprising a pin adapted for disposition within the slot, wherein application of a force within the slot by the pin in a first direction moves the first jaw and the second jaw to the open state, and application of a force within the slot by the pin in a second direction moves the first jaw and the second jaw to the closed state.

4. The surgical clamp combination recited in claim 3, the slot comprising two ramps disposed on opposing sides of the slot.

5. The surgical clamp recited in claim 3, the slot forming a flexible arm on the first jaw, and the first fixed set of teeth being disposed on the flexible arm.

6. The surgical clamp recited in claim 5, the pin being adapted to apply a force on the flexible arm to thereby move the first fixed set of teeth out of mesh with the second fixed set of teeth, and to move the first jaw and the second jaw to one of the open state and the closed state.

7. The surgical clamp recited in claim 3, further comprising:

a flexible arm on the first jaw;

the slot in the first jaw being configured with a straight portion and a curved portion, the straight portion adapted for accommodating the pin and the curved portion providing a reduced thickness of the flexible arm near a bendable area of the flexible arm;

the first fixed set of teeth being disposed on the flexible arm; and the pin being adapted to apply a force on the flexible arm to thereby move the first fixed set of teeth out of mesh with the second fixed set of teeth, and to move the first jaw and the second jaw to one of the open state and the closed state.

8. The surgical clamp recited in claim 3, the first set of fixed set of teeth comprising a pawl, and the second set of fixed teeth comprising a ratchet wheel.

9. The surgical clamp recited in claim 8, the first jaw and the pawl being integrally molded together, and the second jaw and the ratchet wheel being integrally molded together.

10. The surgical clamp recited in claim 9, the first jaw and the second jaw comprising injection molded plastic.

11. A surgical clamp, comprising:

two jaws movable between an open position and a closed position;

a ratchet wheel and pawl assembly connected to the two jaws and adapted for allowing relative rotational movement of the two jaws in a first direction and preventing relative rotational movement of the two jaws in a second direction; and means for disengaging the pawl from the ratchet wheel, to thereby allow for relative rotational movement of the pair of jaws in the second direction.

12. A surgical clamp combination, comprising:

a pair of jaws forming a surgical clamp, the jaws being movable between an open position and a closed position;

a ratchet wheel and pawl assembly connected to the surgical clamp, the ratchet wheel and pawl assembly being adapted for allowing relative movement of the pair of jaws in a first rotational direction and preventing relative movement of the pair of jaws in a second rotational direction;

pawl-removing means for removing the pawl from mesh with the ratchet wheel, to thereby allow for relative movement of the pair of jaws in the second rotational direction;

a clamp applier having a longitudinal axis extending between a proximal end and a distal end;

a tube disposed at the distal end of the clamp applier;

engaging means disposed within the tube for engaging the surgical clamp; and operating means disposed at the proximal end of the clamp applier for operating the engaging means to activate the pawl-removing means to thereby facilitate movement of the pair of jaws in the second rotational direction.

13. The surgical clamp combination recited in claim 12, the surgical clamp comprising an annulus, and the engaging means comprising a hook and a pin, the hook being adapted to be placed within the annulus and the pin being adapted to contact the surgical clamp.

14. The surgical clamp combination recited in claim 13, the surgical clamp comprising a slot for accommodating the pin, the slot having ramps on opposing sides thereof.

15. The surgical clamp combination recited in claim 13, movement of the pin in a first pin direction causing the pair of jaws to move in the first rotational direction, and movement of the pin in a second pin direction activating the pawl-removing means and also causing the pair of jaws to move in the second rotational direction.

16. The surgical clamp combination recited in claim 15, the operating means comprising a trigger for operating the hook and a handle for operating the pin.

17. The surgical clamp combination recited in claim 16, the handle comprising a scissor handle, having one stationary piece and one movable piece.

18. The surgical clamp combination recited in claim 17, further comprising a pivoting arm disposed at a distal end of the tube, the pivoting arm having the pin attached thereto.

19. The surgical clamp combination recited in claim 18, further comprising an actuator spring connected to the pivoting arm, the actuator spring accommodating the pin at a distal end of the actuator spring, the actuator spring being adapted for pivoting with the pivoting arm.

20. The surgical clamp combination recited in claim 18, movement of the movable piece of the scissor handle in a first handle direction rotating the pivoting arm disposed at the end of the tube in a first rotational direction to thereby move the pin in the first direction, and movement of the movable piece of the scissor handle in a second handle direction rotating the pivoting arm disposed at the end of the tube in a second rotational direction to thereby move the pin in the second pin direction.

21. The surgical clamp combination recited in claim 20, wherein movement of the movable piece of the scissor handle in the first handle direction moves the pin in the first pin direction and causes the pair of jaws to close, and wherein movement of the movable piece of the scissor handle in the second handle direction moves the pin in the second pin direction and causes the pair of jaws to open.

22. The surgical clamp combination recited in claim 19, the actuator spring being bendable in a direction approximately normal to the pivoting arm to facilitate movement of the pin on one of the ramps.

23. A surgical clamp having a longitudinal configuration and an axis extending between a proximal end and a distal end of the surgical clamp, the clamp comprising:

a first jaw having a first set of slanted teeth located near the proximal end;

a second jaw having a second set of slanted teeth adapted to be removably placed into mesh with the first set of slanted teeth, the first and second sets of slanted teeth when in mesh being adapted to slide upon one another to thereby allow the first jaw to pivot roughly about the proximal end in a first direction, the first and second sets of slanted teeth when in mesh not allowing the first jaw to pivot roughly about the proximal end in a second direction; and a moving member for moving the first and second sets of slanted teeth out of mesh, to thereby allow the first jaw to pivot roughly about the proximal end in the second direction.

24. A surgical clamp combination, comprising:

a surgical clamp having a longitudinal axis extending between a proximal end and a distal end, and including a supporting structure;

a pair of jaws coupled to the supporting structure, the jaws being movable between an open position and a closed position;

a moving member carried by the supporting structure and operable from near the proximal end of the clamp for moving the jaws between the open position and the closed position, and comprising a ratchet wheel and pawl assembly, which can be selectively engaged and disengaged to facilitate movement of the pair of jaws between the open position and the closed position;

a clamp applier having a longitudinal axis extending between a proximal end and a distal end;

a tube disposed at the distal end of the clamp applier;

an engaging element disposed within the tube for engaging the moving means at the proximal end of the clamp, the engaging means adapted for both selectively engaging and disengaging the ratchet wheel and pawl assembly and for applying forces to the surgical clamp to facilitate movement of the pair of jaws between the open position and the closed position; and an operating member disposed at the proximal end of the clamp applier for operating the engaging element to move the jaws of the clamp.

25. A clamp applier for selectively engaging a surgical clamp and for moving the surgical clamp between an open position and a closed position, the clamp applier having an axis extending between a proximal end and a distal end of the clamp applier, the clamp applier comprising:

a housing disposed at the proximal end;

a tube extending distally of the housing and configured to receive the surgical clamp;

engaging means disposed within the tube and adapted for releasably engaging the surgical clamp;

first moving means disposed near the proximal end and connected to the engaging means, the first moving means being adapted for moving the engaging means between an extended position wherein the engaging means can engage the surgical clamp, and a retracted position wherein the surgical clamp is releasably held in contact with the clamp applier;

operating means disposed within the tube and adapted for releasably engaging the surgical clamp, the operating means being movable in two directions along a line, which is approximately perpendicular to the axis, to thereby move the surgical clamp between the open position and the closed position; and second moving means disposed near the proximal end and connected to the operating means, the second moving means being adapted for moving the engaging means along the line that is approximately perpendicular to the axis.

26. The clamp applier recited in claim 25, the first moving means being activated by a trigger near the proximal end, and the second moving means being activated by a movable handle near the proximal end.

27. A surgical clamp combination, comprising:

a pair of jaws forming a surgical clamp, the jaws being movable between an open position and a closed position;

a ratchet wheel and pawl assembly connected to the surgical clamp, the ratchet wheel and pawl assembly being adapted to permit relative movement of the pair of jaws in a first rotational direction and to prevent relative movement of the pair of jaws in a second rotational direction;

the pawl being removable from the ratchet wheel to thereby allow for relative movement of the pair of jaws in the second rotational direction;

a clamp applier having a longitudinal axis extending between a proximal end and a distal end;

a tube disposed at the distal end of the clamp applier;

an engaging element disposed within the tube for engaging the surgical clamp; and an operating member disposed at the proximal end of the clamp applier for operating the engaging element to remove the pawl from the ratchet wheel and thereby facilitate movement of the pair of jaws in the second rotational direction.

28. The surgical clamp combination recited in claim 27, wherein:

the surgical clamp includes an annulus; and the engaging element of the clamp applier comprises a hook and a pin, the hook being adapted to engage the annulus of the clamp and the pin being adapted to engage the pawl of the clamp.

29. The surgical clamp combination recited in claim 28, further comprising:

a pivoting arm disposed at a distal end of the tube, the arm being pivotal generally in a pivot plane; and the pin of the engaging element being attached to the pivoting arm.

30. The surgical clamp combination recited in claim 29, further comprising:

an actuator spring connected to the pivoting arm; and the actuator spring being coupled to the pin and being adapted for pivotal movement with the pivoting arm.

31. The surgical clamp combination recited in claim 30, wherein:

the actuator spring is bendable in a direction generally normal to the pivot plane of the pivoting arm.

32. A surgical clamp, comprising:

a first jaw of the clamp having a proximal end and a distal end, the first jaw having a first set of teeth located near the proximal end of the first jaw;

a second jaw of the clamp having a proximal end and a distal end, the second jaw having a second fixed set of teeth located near the proximal end of the second jaw;

at least the first jaw being movable between a first position wherein the first set of teeth are spaced from the second set of teeth, and a second position wherein the first set of teeth mesh with the second set of teeth;

at least one of the first jaw and the second jaw being movable when the first jaw is in the second position, between an open state wherein the distal end of the first jaw is spaced from the distal end of the second jaw to accept a body conduit, and a closed state wherein the distal end of the first jaw is proximate to the distal end of the second jaw to at least partially occlude the body conduit; and a surgical clamp actuator operable to permit movement of the surgical clamp between a disengaged position wherein the clamp is free of the clamp actuator, and an engaged position wherein the clamp is coupled to the clamp actuator, the clamp actuator being operable in the engaged position to move the clamp between the open state and the closed state.

33. The surgical clamp assembly recited in claim 32, the first jaw of the clamp being rotatably secure to the second jaw of the clamp in proximity to the first set of teeth and second set of teeth, so that the first set of teeth and the second set of teeth can be moved between the first position and the second position.

34. The surgical clamp assembly recited in claim 33 wherein at least one of the first jaw and the second jaw of the clamp defines a slot; and the surgical clamp actuator further comprises a pin adapted for disposition within the slot, the pin in the slot being movable in a first direction to move the first jaw relative to the second jaw toward the open state, and being movable in a second direction opposite to the first direction to move the first jaw relative to the second jaw toward the closed state.

35. The surgical clamp assembly recited in claim 34 wherein the slot of the clamp is defined by a pair of ramps disposed on opposing sides of the slot.

* * * * *